United States Patent [19]
Kellner et al.

[11] Patent Number: 5,525,347
[45] Date of Patent: Jun. 11, 1996

[54] COMPOSITION AND METHODS FOR TREATING PERFORMANCE ANXIETY

[75] Inventors: Charles H. Kellner, Sullivans Island; Cherry W. Jackson; C. Lindsay DeVane, both of Mt. Pleasant, all of S.C.

[73] Assignee: Medical University of South Carolina, Charleston, S.C.

[21] Appl. No.: 381,114

[22] Filed: Jan. 31, 1995

[51] Int. Cl.$^6$ .................................. A01N 25/34
[52] U.S. Cl. ................ 424/408; 424/409; 514/406; 514/408; 514/411; 514/421; 514/510; 514/553; 514/556; 514/557; 514/569; 514/642; 514/959; 514/962
[58] Field of Search .................... 514/406, 408, 514/411, 421, 510, 553, 556, 557, 569, 642, 959, 962; 424/408, 409

[56] References Cited

U.S. PATENT DOCUMENTS

| | | | |
|---|---|---|---|
| 4,931,430 | 6/1990 | Sudilovsky et al. | 514/19 |
| 4,962,128 | 10/1990 | Doogan et al. | 514/647 |
| 5,089,502 | 2/1992 | Sudilovsky et al. | 514/274 |
| 5,166,202 | 11/1992 | Schweizer | 514/220 |
| 5,168,099 | 12/1992 | Iwata et al. | 514/452 |
| 5,371,082 | 12/1994 | Versiani et al. | 514/237.8 |
| 5,447,952 | 9/1995 | Wulfert et al. | 514/424 |
| 5,457,121 | 10/1995 | Schaus et al. | 514/412 |

OTHER PUBLICATIONS

The Handbook of Psychiatric Drug Threapy, Little, Brown and Co., Boston/Toronto, Pub., Ch. 7, p. 142, 1987.
The Phychiatric Drug Handbook, Mosby Year Book, Pub., Ch. 7, pp. 247–248, 1992.
Physicians' Desk Reference®, 48 Edition, pp. 1900–1902 and 2540–2542, 1994.
The Micromedex Inc. database, vol. 70, Exp. Feb. 28, 1994, "Drug Consults: Hyperhidrosis—Drug Therapy".
The Micromedex Inc. database, vol. 70, Exp. Feb. 28, 1994, "Drug Evaluation Monograph Topic: Glycopyrrolate".
Uhde et al., "Phenomenology and Neurobiology of Social Phobia: Comparison With Panic Disorder,"*J. Clin. Psych.* 52(suppl):31–40, Nov. 1991.
Liebowitz et al., "Social Phobia," *Arch. Gen. Psychiatry* 42:729–736, Jul. 1985.
Hartley et al., "The Effect of Beta Adrenergic Blocking Drugs on Speakers' Performance and Memory," *Brit. J. Psychiatry* 142:512–517, 1983.
James et al., "Effect of Oxprenolol on Stage–Fright in Musicians," *Lancet* ii:952–954, Nov. 5, 1977.
Brewer C, "Beneficial Effect of Beta–Adrenergic Blockade on 'Exam, Nerves'," *Lancet* ii:435, Aug. 26, 1972.

*Primary Examiner*—Samuel A. Acquah
*Attorney, Agent, or Firm*—Needle & Rosenberg

[57] ABSTRACT

The invention provides a pharmaceutical composition for treating performance anxiety and social phobia comprising a therapeutic amount for the treatment of a patient of a β-adrenergic receptor blocking compound and an anti-diaphoretic compound. The preferred β-adrenergic receptor blocking compound is the lipophilic β-blocker propranolol HCL. The anti-diaphoretic compound of the present invention is preferably glycopyrrolate. The composition for treating performance anxiety and social phobia can further include a pharmaceutically acceptable carrier. A method of preventing or treating performance anxiety or social phobia in a patient comprising administering the composition of the invention to a patient in need of such treatment is also provided. The composition administered in the present method comprises a therapeutic amount of a β-adrenergic receptor blocking compound and an anti-diaphoretic compound.

27 Claims, No Drawings

COMPOSITION AND METHODS FOR TREATING PERFORMANCE ANXIETY

BACKGROUND OF THE INVENTION

1. Statement of the Invention

The present invention is directed to the treatment of performance anxiety. More specifically the invention provides a composition and method for treating performance anxiety.

2. Background Art

Many people experience a "normal" fear of public speaking. However, for some people that fear that he or she may do something or act in a way that will be humiliating or embarrassing is sufficient to cause avoidance behavior to the point of interfering with occupational or social functioning. In this situation, a diagnosis of performance anxiety may be appropriate. Public speaking is the most common fear in social phobia (Uhde et al., 1991), followed by eating in public, writing in public, and using public lavatories.

Social phobia is one of several major anxiety disorders and can constitute a chronic and disabling illness. There is currently no FDA approved treatment for social phobia although case reports suggest efficacy for several drug classes (the beta adrenergic receptor blockers, including propranolol hydrochloride (10–120 mg) (The Handbook of Psychiatric Drug Therapy, (Little, Brown and Co., Boston/Toronto, Pub., Ch. 7, p. 142) and The Psychiatric Drug Handbook, (Mosby Year Book, Pub., Ch. 7, pp. 247–248) benzodiazepines; and monoamine oxidase inhibitors).

Social phobia is one of seven major anxiety disorders. It is felt to be a discrete and separate illness from panic disorder or generalized anxiety disorder (Liebowitz et al., 1985). Its essential feature is a persistent fear of one or more situations (the social phobic situations) in which the person is exposed to possible scrutiny by others and fears that he or she may do something or act in a way that will be humiliating or embarrassing. Social phobia results in marked anticipatory anxiety when an affected person is confronted with the need to enter into a phobic situation.

The magnitude of this problem is unknown, but estimates of prevalence range from 0.9% to 2.6% of urban populations (Liebowitz et al., 1985). Social phobia may often co-exist with panic disorder (Stein et al., 1989). In one report, nearly one-half (46%) of a group of patients with panic disorder had concomitant diagnoses of social phobia. The importance of social phobia is emphasized by limited data which suggest a high morbid risk for major depression and alcoholism in this population. The disorder is chronic and can be disabling.

Social phobia in general, and performance anxiety in particular, are among the most neglected major anxiety disorders in terms of treatment. Pharmacotherapy has focused on trials of monoamine oxidase inhibitors (MAOIs) (Liebowitz et al., 1985). Few reports have resulted from controlled clinical trials. The β-blockers have shown some efficacy, generally on performance anxiety when a peripheral component was central to the phobic situation (e.g. musical performance)(Brewer C, *Lancet* ii:435, 1972; Hartley et al., *Brit. J. Psychiatry* 142:512–517, 1983; James et al., *Lancet* ii:952–954, 1977). The MAOIs have well recognized drawbacks to their use (side effects, dietary restrictions) and the benzodiazepines have the disadvantage of dependence liability, further complicating use in patients with alcohol abuse. No reports have been published where the symptom of sweating as an anxiety symptom associated with public speaking was specifically targeted for treatment. Thus, there exists a need for a safe, effective medication for the treatment of both the anxiety and sweating associated with performance anxiety.

The present invention meets this need by providing a fixed-dose combination of a β-blocker and an anti-diaphoretic in a single dosage form effective to treat specific anxiety symptoms associated with the performance anxiety of public speaking. It is anticipated that selected patients with social phobia related to other performance tasks would also benefit. Propranolol hydrochloride controls palpitations, tachycardia, tremor and voice quavering while glycopyrrolate controls diaphoresis (sweating). These two medications have never previously been combined in a single pill. This medication provides, in a convenient form, a type of comprehensive medical treatment for anxiety symptoms that has not been previously available.

SUMMARY OF THE INVENTION

The invention provides a pharmaceutical composition for treating performance anxiety or social phobia comprising a therapeutic amount for the treatment of a patient of a β-adrenergic receptor blocking compound and an anti-diaphoretic compound. The preferred β-adrenergic receptor blocking compound is the lipophilic β-blocker propranolol HCL. The anti-diaphoretic compound of the present invention is preferably glycopyrrolate. The composition for treating performance anxiety and social phobia can further include a pharmaceutically acceptable carrier, diluent or excipient.

A method of preventing or treating performance anxiety in a patient comprising administering the composition of the invention to a patient in need of such treatment is also provided. The composition administered in the present method comprises a therapeutic amount of a β-adrenergic receptor blocking compound and an anti-diaphoretic compound.

DETAILED DESCRIPTION OF THE INVENTION

The invention provides a pharmaceutical composition for treating performance anxiety or social phobia comprising a therapeutic amount for the treatment of a patient of a β-adrenergic receptor blocking compound and an anti-diaphoretic compound.

The β-adrenergic receptor blocking compound of the composition (hereinafter "β-blocker") can be one that crosses the blood brain barrier. The lipophilic β-blocker propranolol HCL is one example of a β-blocker that crosses the blood brain barrier. Other examples of lipophilic β-blockers include metoprolol succinate (TOPROL XL™, Astra, Wesboro, Mass.; Merck Index, page 881; Brandstrom et al. U.S. Pat. No. 3,873,600), and nadolol (Merck Index, page 909; Hauck et al. U.S. Pat. No. 3,935,267). The β-blocker can alternatively be one that does not cross the blood brain barrier. For example, atenolol (TENORMIN®, Zeneca, Wilmington, Del.; Merck Index, page 124; Barrett et al. U.S. Pat. Nos. 3,663,607 and 3,836,671) acts primarily on the peripheral nervous system. Other β-blockers include but at not limited to the following:

sotalol HCL (BETAPACE® Berley Laboratories, Wayne, N.J.);

timolol maleate (BLOCADREN® Merck & Co., Inc., West Point, Pa.)

esmolol HCL (BREVIBLOC® Anaquest Inc., Liberty Corner, N.J.)

carteolol HCL (CARTROL® Abbott Laboratories, Chicago, Ill.)

betaxolol HCL (KERLONE® G.D. Searle & CO., Chicago, Ill.)

penbutolol sulfate (LEVATOL® Reed & Carnrick, Marina Del Rey, Calif.)

metoprolol tartrate (LOPRESSOR® Geigy Pharmaceuticals, Ardsley, N.Y.)

acebutolol HCL (SECTRAL® Wyeth-Ayerst Laboratories, Philadelphia, Pa.)

pindolol (VISKEN® Sandoz Pharmaceuticals Corp., East Hanover, N.J.)

bisoprolol fumorate (ZEBETA™ Lederle Laboratories, Wayne, N.J.)

β-blockers as a class of compounds are expected to be effective in the present composition, because they act through the same mechanism in the subject's nervous system. Routine methods for screening compounds for their β-blocking activity and for determining which β-blockers cross the blood-brain barrier are known in the art (Spahn-Langguth et al. "Improved enantiospecific RP-HPLC assays for propranolol in plasma and urine with pronethalol as internal standard". *Journal of Analytical Toxicology*, 15(4):209–213, 1991; Sproat and Lopez "Around the beta-blockers, one more time, "Review *DICP* 25(9):962–971, 1991; and Davies, C. "Chromatography of beta-adrenergic blacking agents," Review *Journal of Chromatography* 531:131–180, 1990). Thus, given the teaching of the present invention, it is contemplated that other β-blockers, whether presently known or later developed, are within the scope of the invention.

An exemplary method of making propranolol HCl is provided in Example 1. Furthermore, this β-blocker is well known in the art and is commercially available (INDERAL®, Ayerst, New York, N.Y.). Other β-blockers are also commercially available, and the synthesis of β-blockers is taught as referenced in the Merck Index entries for the compounds.

The anti-diaphoretic compound of the present invention is preferably an anticholinergic compound that does not cross the blood brain barrier, and, thus, acts only on the peripheral nervous system. Glycopyrrolate is an example of an anticholinergic compound that does not cross the blood brain barrier. It is expected that other anticholinergic compounds that act only peripherally will also be effective in the present composition. Thus, other peripherally acting anticholinergic compounds whether presently known or subsequently produced are within the scope of the present invention. Additionally, although not the most preferred, centrally acting anticholinergics (e.g., atropine, Merck Index, page 125) can also be used in the present method and composition. Routine methods for screening compounds for their anticholinergic activity and for their ability to cross the blood-brain barrier are well known (for example, see Ali-Melkkila et al. "Pharmacokinetics and related pharmacodynamics of anticholinergic drugs," Review, *Acta Anaestesiologica Scandinavica* 37(7):633–642, 1993).

An exemplary method of making glycopyrrolate is provided in Example 1. Furthermore, this anticholinergic compound is well known in the art and is commercially available (ROBINUL®, A. H. Robins, Richmond, Va.).

Thus, in a preferred embodiment of the present composition, the β-adrenergic receptor blocking compound is propranolol HCl and the anti-diaphoretic compound is glycopyrrolate. In this composition, the propranolol HCL is preferably in an amount of from 5 to 40 mg and the glycopyrrolate can be in an amount of from 0.25 to 1.0 mg. In a preferred composition, the propranolol HCl is in an amount of about 5 mg and the glycopyrrolate is in an amount of about 0.25 mg. Thus, one of the advantages of the present composition and method is the effectiveness of the components at low dosages compared to other uses of the same compounds. Lower dosages, for example as low as 3 mg of β-blocker and as low as 0.1 mg of anticholinergic are within the scope of the invention once routinely determined by the skilled practitioner to be effective in a given patient. Other dosages within the disclosed range will also be effective, but may be attended by tolerable side affects that are avoided at the lower dosages. For example, the propranolol HCl can be in an amount of about 30 mg and the glycopyrrolate can be in an amount of about 1.0 mg.

The composition for treating performance anxiety and social phobia can further include a pharmaceutically acceptable carrier. The compositions can also include other medicinal agents, pharmaceutical agents, carriers, adjuvants, diluents, etc. By "pharmaceutically acceptable" is meant a material that is not biologically or otherwise undesirable, i.e., the material may be administered to an individual along with the selected compound without causing any undesirable biological effects or interacting in a deleterious manner with any of the other components of the pharmaceutical composition in which it is contained. For example, the carrier can be cornstarch. Examples of other excipients or carriers include compositions of one or more of lactose, magnesium stearate, microcrystalline cellulose and stearic acid, povidone, dibasic calcium phosphate and sodium starch glycolate. As the preferred mode of administration is oral, it is contemplated that any carrier suitable for oral administration can be the carrier of the present composition. If other modes of administration are used, carriers will be selected using standard criteria for the administration of compositions by that mode.

Because the preferred method of administration of the present compound is oral, the composition can be contained in a gelatin capsule, tablet, liquid or powder, etc for ingestion. For oral administration, fine powders or granules may contain diluting, dispersing, and/or surface active agents, and may be presented in water or in a syrup, in capsules or sachets in the dry state, or in a nonaqueous solution or suspension wherein suspending agents may be included, in tablets wherein binders and lubricants may be included, or in a suspension in water or a syrup. Where desirable or necessary, flavoring, preserving, suspending, thickening, or emulsifying agents may be included. Tablets and capsules are preferred oral administration forms, and these may be coated. Actual methods of preparing such dosage forms are known, or will be apparent, to those skilled in this art; for example, see *Remington's Pharmaceutical Sciences* (18th Ed., E. W. Martin (ed.), Mack Publishing Co., Easton, Pa.).

A method of treating performance anxiety in a patient comprising administering the composition of the invention to a patient in need of such treatment is also provided. As described above, the composition administered in the present method comprises a therapeutic amount of a β-adrenergic receptor blocking compound and an anti-diaphoretic compound. More preferably, the method of treating performance anxiety in a patient comprises administering to a patient in need of such treatment the composition in which the β-adrenergic receptor blocking compound is propranolol HCl and the anti-diaphoretic compound is glycopyrrolate. Preferably, the propanolol HCL is in an amount of about 5 mg and the glycopyrrolate is in an amount of about 0.25 mg. However, other amounts of the compounds can be administered in accordance with the above description of the composition of the invention.

The invention also provides a method of preventing performance anxiety in a patient by administering the composition comprising a therapeutic amount of a β-adrenergic receptor blocking compound and an anti-diaphoretic compound to a patient in need of such preventive treatment. More preferably, the method of preventing performance anxiety in a patient comprises administering to a patient in need of such preventive treatment the composition in which the β-adrenergic receptor blocking compound is propranolol HCl and the anti-diaphoretic compound is glycopyrrolate. Preferably, the propanolol HCL is in an amount of about 5 mg and the glycopyrrolate is in an amount of about 0.25 mg. However, other amounts of the compounds can be administered in accordance with the above description of the composition of the invention.

A method of treating or preventing social phobia in a patient is also provided. This method comprises the step of administering the composition comprising a therapeutic amount of a β-adrenergic receptor blocking compound and an anti-diaphoretic compound to a patient in need of such prevention or treatment. More preferably, the method of preventing or treating social phobia in a patient comprises administering to the patient the composition in which the β-adrenergic receptor blocking compound is propranolol HCl and the anti-diaphoretic compound is glycopyrrolate. Preferably, the propanolol HCL is in an amount of about 5 mg and the glycopyrrolate is in an amount of about 0.25 mg. However, other amounts of the compounds can be administered in accordance with the above description of the composition of the invention.

Because the invention teaches that performance anxiety can be treated or prevented using the compositions taught herein, the invention also provides a method of preventing or treating performance anxiety in a patient by administering a therapeutic amount of a β-adrenergic receptor blocking compound and administering, either before, after, or simultaneous to the administration of the β-adrenergic receptor blocking compound, a therapeutic amount of an anti-diaphoretic compound to a patient in need of such prevention or treatment. In this method, the β-adrenergic receptor blocking compound can be propranolol HCl and the anti-diaphoretic compound can be glycopyrrolate. The amounts administered can be as described above for the compositions of the invention.

The invention also provides a method of preventing or treating social phobia in a patient comprising the step(s) of administering a therapeutic amount of a β-adrenergic receptor blocking compound and administering, either before, after, or simultaneous to the administration of the β-adrenergic receptor blocking compound, a therapeutic amount of an anti-diaphoretic compound to a patient in need of such treatment. In this method, the β-adrenergic receptor blocking compound can be propranolol HCl and the anti-diaphoretic compound can be glycopyrrolate. The amounts administered can be as described above for the compositions of the invention.

As described above, the preferred mode of administration in the present method is oral. The dosage form administered can be selected from among the standard oral dosage forms depending on the circumstances of the patient in need of the present treatment or prevention methods. Actual methods of preparing such dosage forms are known, or will be apparent, to those skilled in this art; for example, see *Remington's Pharmaceutical Sciences* (18th Ed., E. W. Martin (ed.), Mack Publishing Co., Easton, Pa.).

The following examples are intended to illustrate, but not limit, the invention. While the protocols described are typical of those that might be used, other procedures known to those skilled in the art may be alternatively employed.

EXAMPLES

Example 1

Preparation of the Compositions

A pharmaceutical composition for the treatment of performance anxiety is a combination of propranolol HCL and glycopyrrolate. These two drugs are combined with carriers or excipients, for example, a cornstarch excipient in a gelatin capsule. The form of the composition can vary within the parameters known in the art as described herein.

Propranolol Hydrochloride 2-propranolol, 1-[(1-methylethyl)amino]-3-(1 -naphthakenyloxy)-hydrochloride; Inderal (Ayerst). 1-(Isopropylamino)-3-(1-napthyloxy)-2-propanol hydrochloride (318-98-9) $C_{16}H_{21}NO_2 \cdot HCl$(295.81) (Osol A. Remington's Pharmaceutical Sciences 16th ed. Mack Publishing Company, Easton, Pa. 18042 1980:845–6)

Preparation: alpha-Naphthol is reacted with epichlorohydrin in aqueous alkali to form 2,3-epoxypropyl alpha-naphthyl ether. The epoxy ring is ruptured by reaction with isopropylamine. The base is converted Lo hydrochloride with HCl.

Description: White or almost white powder that is odorless and has a bitter taste. It is stable to heat, unstable in light and nonhygroscopic. It melts at about 161 degrees and has a pKa of 9.45.

Solubility: 1 g in 20 ml water and 20 ml alcohol; slightly soluble in chloroform; practically insoluble in ether.

Glycopyrrolate

Pyrrolidinium, 3-(cyclopenthylhydroxyphenylacetyl)oxy-1, 10 dimethylbromide; Robinul (Robins). 3-Hydroxyl-1,1-dimethylpyrrolidinum bromide -cyclopentylmandelate (596-51-0) $C_{19}H_{28}BRNO_3$ (398.34). (Osol A. Remington's Pharmaceutical Sciences 16th ed. Mack Publishing Company, Easton, Pa. 18042 1980:855.

Preparation: alpha-Phenylcyclopentaneglycolic acid is esterified by refluxing with methanol in the presence of hydrochloric acid and the resulting ester is transesterified with 1-methyl-3-pyrrolidinol using sodium as a catalyst. The transester is then reacted with methyl bromide to give glycopyrrolate.

Description: White, crystalline powder that is odorless and has a bitter taste; stabile in light and heat and nonhygroscopic; melts within a range of 2 degrees between 193 degrees and 198 degrees.

Solubility: 1 g in 4.2 ml water, 30 ml alcohol, 260 ml chloroform, insoluble in ether.

Example 2

Efficacy Shown in Open Clinical Trial

Protocol

Subjects were selected based on their history of experiencing performance anxiety in the context of public speaking. Subjects received oral doses of the present composition (propranolol≈10 mg and glycopyrrolate≈0.25 mg) at various times prior to speaking engagements. The parameters measured included the following: diaphoresis, anxiety and side effects (e.g., dry mouth).

Subject 1, a forty-one year old male, ingested two test doses on different occasions and reported good anti-anxiety effect on both occasions. When he ingested the medication two hours prior to public speaking, there was a more marked anti-diaphoretic effect than when the medication was ingested one hour before the speaking engagement.

Subject 2, a thirty-seven year old female, also took two doses of the medication on two separate occasions. When she ingested the medication one and a half hours before the public speaking engagement, she reported some calming effect and some effect on controlling diaphoresis. The other dose that she took only forty minutes before the public speaking engagement did not control her diaphoresis as well.

Subject 3, a thirty-one year old male, took a test dose the day before a public speaking engagement and noted no side effects. He took a second dose that consisted of 10 mg of propranolol HCL and 0.25 mg of glycopyrrolate the subsequent day, two hours prior to a speaking engagement, and noted excellent anti-anxiety and anti-diaphoretic effect.

Subject 4, a thirty-two year old male, ingested a single dose of the combination one hour prior to a public speaking engagement and noted good anti-anxiety and diaphoresis control, but remarked that he had mild dry mouth as a side effect.

Example 3

Large Scale Clinical Trial

The present study is an open-label, variable dose clinical trial to assess the efficacy and safety of two fixed doses of combined glycopyrrolate and propranolol HCL in the treatment of performance anxiety. Up to fifty volunteers who have given informed consent, take either 5 mg of propranolol HCL hydrochloride combined with 0.25 mg of glycopyrrolate or 10 mg of propranolol HCL combined with 0.25 mg of glycopyrrolate either once or twice over a period of two hours preceding a performance task. The task is an occasion of public speaking that the subject anticipates will be highly anxiety-producing.

Subjects can vary the dose according to need in the range of one capsule of the lower strength up to a maximum of two capsules of the higher strength formulation. Subjects act as their own controls and complete a subjective evaluation of drug effects and anxiety state before and after the performance task. The results of the study are expected to verify the results of the study described in Example 1 that combined glycopyrrolate and propranolol HCL is an effective treatment for reducing anxiety and enhancing performance associated with events that provoke anxiety in the patient.

Several anxiety rating scales are in common use in anxiety research (Marks et al. *Behav. Res. Ther.* 17:263–267, 1982; Davidson et al. *J. Clin. Psych.* 52(suppl):48–51, 1991). Patients complete a series of self evaluations before and after their performance task. Scores are computed as a percentage change from baseline on various dimensions of anxiety. Descriptive statistics are calculated for changes in anxiety ratings between baseline and final analysis. The presence of side effects, such as dry mouth, light-headedness, nausea and difficulty urinating, will be specifically sought.

Throughout this application various publications are referenced within parentheses. The disclosures of these publications in their entireties are hereby incorporated by reference into this application in order to more fully describe the state of the art to which this invention pertains.

What is claimed is:

1. A pharmaceutical composition for treating performance anxiety or social phobia comprising a therapeutic amount for the treatment of a patient of a β-adrenergic receptor blocking compound and an anti-diaphoretic compound.

2. The composition of claim 1, wherein the β-adrenergic receptor blocking compound is propranolol HCl.

3. The composition of claim 1, wherein the anti-diaphoretic compound is an anti-cholinergic compound.

4. The composition of claim 1, wherein the anti-diaphoretic compound is glycopyrrolate.

5. The composition of claim 1, wherein the β-adrenergic receptor blocking compound is propranolol HCl and the anti-diaphoretic compound is glycopyrrolate.

6. The composition of claim 5, wherein the propranolol HCl is in an amount of from 5 to 40 mg and the glycopyrrolate is in an amount of from 0.25 to 1.0 mg.

7. The composition of claim 5, wherein the propranolol HCl is in an amount of about 5 mg and the glycopyrrolate is in an amount of about 0.25 mg.

8. The composition of claim 5, wherein the propranolol HCl is in an amount of about 30 mg and the glycopyrrolate is in an amount of about 1.0 mg.

9. The composition of claim 1, wherein the composition further includes a pharmaceutically acceptable carrier.

10. The composition of claim 9, wherein the carrier is cornstarch.

11. The composition of claim 1, wherein the composition is contained in a gelatin capsule.

12. A method of treating performance anxiety in a patient comprising the step of administering the composition of claim 1 to a patient in need of such treatment.

13. A method of treating performance anxiety in a patient comprising the step of administering the composition of claim 5 to a patient in need of such treatment.

14. A method of preventing performance anxiety in a patient comprising the step of administering the composition of claim 1 to a patient in need of such treatment.

15. A method of preventing performance anxiety in a patient comprising the step of administering the composition of claim 5 to a patient in need of such treatment.

16. A method of treating social phobia in a patient comprising the step of administering the composition of claim 1 to a patient in need of such treatment.

17. A method of treating social phobia in a patient comprising the step of administering the composition of claim 5 to a patient in need of such treatment.

18. A method of preventing social phobia in a patient comprising the step of administering the composition of claim 1 to a patient in need of such treatment.

19. A method of preventing social phobia in a patient comprising the step of administering the composition of claim 5 to a patient in need of such treatment.

20. A method of treating performance anxiety in a patient comprising the step(s) of administering a therapeutic amount of a β-adrenergic receptor blocking compound and administering, either before, after, or simultaneous to the administration of the β-adrenergic receptor blocking compound, a therapeutic amount of an anti-diaphoretic compound to a patient in need of such treatment.

21. The method of claim 20, wherein the β-adrenergic receptor blocking compound is propranolol HCl and the anti-diaphoretic compound is glycopyrrolate.

22. A method of preventing performance anxiety in a patient comprising the step(s) of administering a therapeutic amount of a β-adrenergic receptor blocking compound and administering, either before, after, or simultaneous to the administration of the β-adrenergic receptor blocking compound, a therapeutic amount of an anti-diaphoretic compound to a patient in need of such treatment.

23. The method of claim 22, wherein the β-adrenergic receptor blocking compound is propranolol HCl and the anti-diaphoretic compound is glycopyrrolate.

24. A method of treating social phobia in a patient comprising the step(s) of administering a therapeutic amount of a β-adrenergic receptor blocking compound and administering, either before, after, or simultaneous to the administration of the β-adrenergic receptor blocking compound, a therapeutic amount of an anti-diaphoretic compound to a patient in need of such treatment.

25. The method of claim 24, wherein the β-adrenergic receptor blocking compound is propranolol HCl and the anti-diaphoretic compound is glycopyrrolate.

26. A method of preventing social phobia in a patient comprising the step(s) of administering a therapeutic amount of a β-adrenergic receptor blocking compound and administering, either before, after, or simultaneous to the administration of the β-adrenergic receptor blocking compound, a therapeutic amount of an anti-diaphoretic compound to a patient in need of such treatment.

27. The method of claim 26, wherein the β-adrenergic receptor blocking compound is propranolol HCl and the anti-diaphoretic compound is glycopyrrolate.

* * * * *